(12) United States Patent
Schumann et al.

(10) Patent No.: US 6,949,512 B1
(45) Date of Patent: Sep. 27, 2005

(54) THERAPEUTIC AGENT FOR THE TREATMENT OF SEPTICAEMIA ITS PREPARATION AND USE

(75) Inventors: Ralf Reiner Schumann, Zepernick (DE); Norbert Lamping, New York, NY (US)

(73) Assignee: Max-Delbruck-Zentrum fur Molekulare Medizin, Berlin (DE)

( * ) Notice: Subject to any disclaimer, the term of this patent is extended or adjusted under 35 U.S.C. 154(b) by 0 days.

(21) Appl. No.: 09/484,121

(22) Filed: Jan. 13, 2000

Related U.S. Application Data

(63) Continuation of application No. PCT/DE98/00964, filed on Apr. 4, 1998.

(30) Foreign Application Priority Data

Jul. 11, 1997 (DE) ................. 197 29 810

(51) Int. Cl.[7] .................. A61K 38/00; A61K 49/00
(52) U.S. Cl. ............... 514/12; 514/8; 514/14; 514/15; 514/21; 530/350; 435/69.5; 435/69.7; 435/235.1; 435/320.1; 424/9.1
(58) Field of Search ............... 514/12, 8, 14, 514/15, 21; 530/350; 435/69.7, 235.1, 320.1, 435/69.5; 424/9.1

(56) References Cited

U.S. PATENT DOCUMENTS 5,990,082 A * 11/1999 Dedrick et al. ........... 514/8

FOREIGN PATENT DOCUMENTS

| WO | WO 94/25476 | * 11/1994 | |
|---|---|---|---|
| WO | WO-9425476 A1 | * 11/1994 | .......... C07H 15/12 |
| WO | WO 95/08560 | * 3/1995 | |
| WO | WO-9508560 A1 | * 3/1995 | ............ C07K 1/02 |

OTHER PUBLICATIONS

Lamping, et al., Immune consequences Trauma, Shoc Sepsis, Int. Congr. 4th (1997) 15-19.*
Gazzano-Santoro et al., Infection and Immunity. 62, 1185-1191 (1994).*
Su et al., J Immunology 153, 743-752 (1994).*
Lamping et al., J Clin. Invest. 101, 2065-2071 (1998).*
Schumann et al., Science 249 (4975) 1429-1431 (1990).*
Lengacher et al. Reactivity of murine and human recombinant LPS binding protein (LBP) within LPS and gram negative bacteria. J. Inflammation 47, 165-172 (1995/1996).*
Lengachev et al., J. Inflammation 47, 165-172 (1995/1996).*
Zweigner et al., Blood 96 (13), 3800-3808 (Dec. 2001).*

* cited by examiner

*Primary Examiner*—Jon Weber
*Assistant Examiner*—Chih-Min Kam
(74) *Attorney, Agent, or Firm*—Goodwin Procter LLP

(57) ABSTRACT

A therapeutic agent for the treatment of septicemia, its preparation and use, with application in the pharmaceutical industry and medicine. This therapeutic agent contains essential element, the lipopolysaccharide binding protein (LBP). Also disclosed are LBP variants, mutants and hybrid proteins. Murine or rabbit LBP may also be used, besides human LBP.

3 Claims, 7 Drawing Sheets

THERAPEUTIC AGENT FOR THE TREATMENT OF SEPTICAEMIA ITS PREPARATION AND USE

This application is a continuation of PCT/DE98/00964, filed Apr. 4, 1998, which claims the benefits of foreign priority of German Application No. 19729810.9, filed Jul. 11, 1997.

FIELD OF INVENTION

The invention relates to a therapeutic agent for the treatment of septicemia, its preparation and use. Fields of application of the invention are pharmaceutical industry and medicine.

BACKGROUND

Septicemia with its frequently lethal complications is one of the clinical syndromes in medicine feared most. It is therapeutically not controllable, claiming a few 100,000 casualties a year alone in the Western countries. New treatment options have to be looked for as antibiotics act too slowly, not preventing the release of bacterial toxins, partly even intensifying it. Pouring out of messenger substances (cytokines) by the host organism released by bacterial toxins is the most important element of the pathogenetic cascade leading to the clinical picture of septicemia. Various new therapeutic approaches, on the one hand, blocking of bacterial lipopolysaccharide (LPS) as the most important toxin by antibodies or antagonizing the endogenous, so-called proinflammatory cytokines failed completely in comprehensive clinical studies (C. Natanson et al., Ann. Intern Med. 120, 771–783 (1994).

SUMMARY OF THE INVENTION

The invention is based on the task to develop a therapeutic agent for the treatment of septicemia.

This task was solved by an agent containing the protein LBP binding lipopolysaccharide as basic component.

The characteristic features of the invention are contained claims 1–11. It is possible to use also murine or rabbit LBP apart from human LBP.

DETAILED DESCRIPTION

Figure 1:
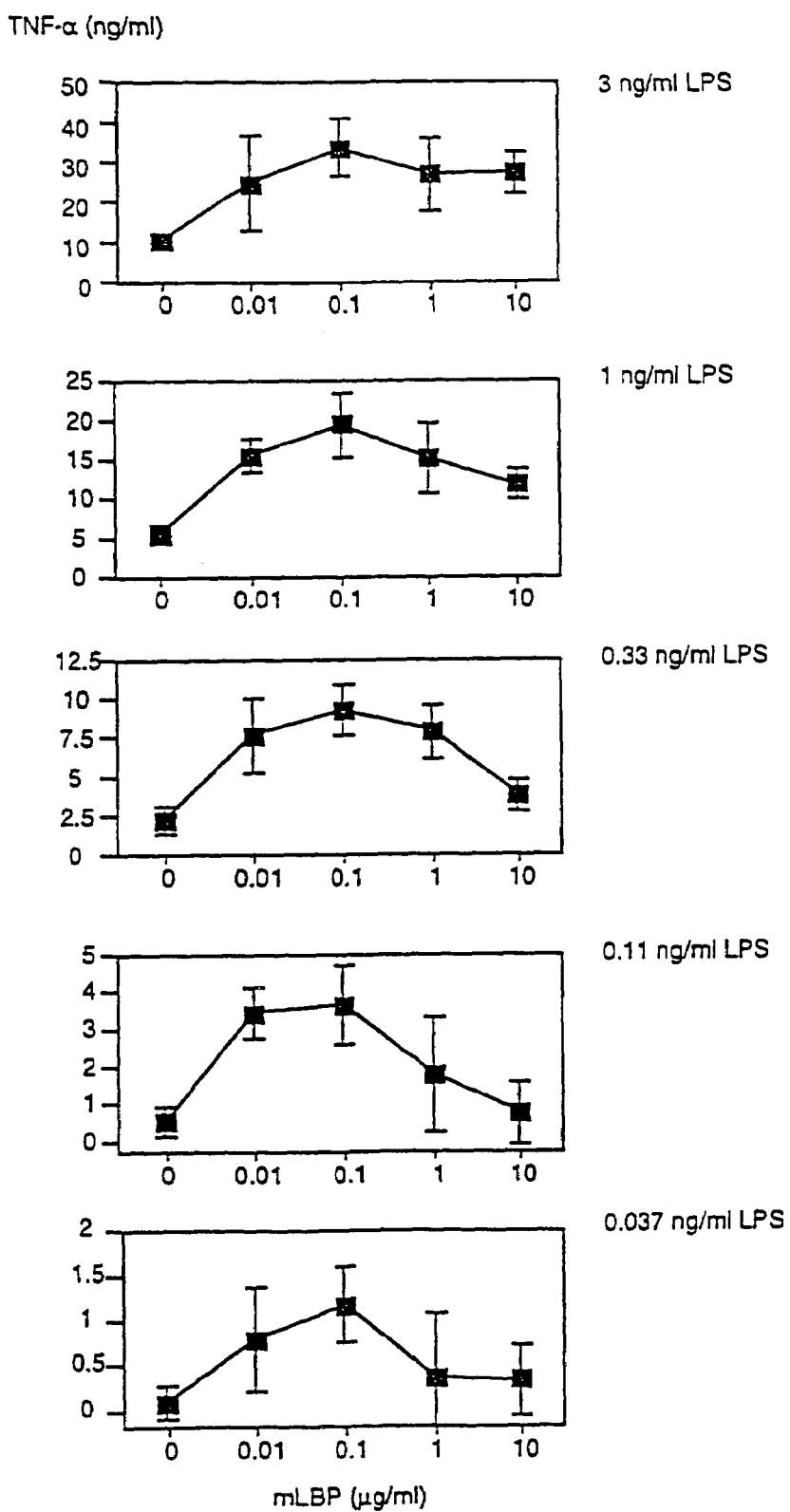
FIG. 1: A murine macrophage cell line is stimulated in vitro with various concentrations of the bacterial toxin LPS for synthesizing the septicemia mediator TNF depending on LBP. In the case of high LPS concentrations not occurring in the organism LBP does not affect the synthesis of TNF. However, the stimulation of macrophages by lower LPS quantities is inhibited by high LBP concentrations as they occur in vivo during the acute phase and may be also achieved by an exogenous addition of LBP.
Figure 2:
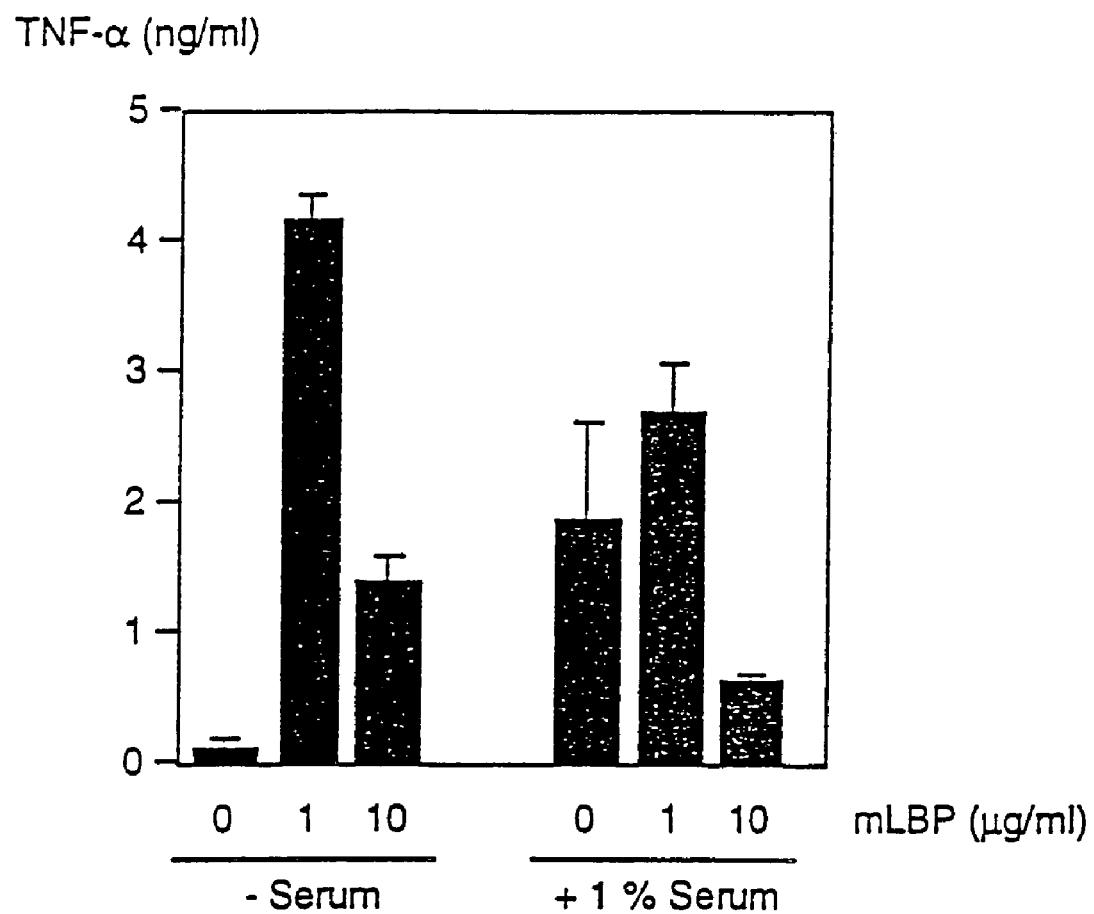
FIG. 2: Here it appears that the addition of LBP in the presence of serum suppresses the production of TNF by the macrophage cell line. LBP contained in serum is responsible for this effect.
Figure 3:
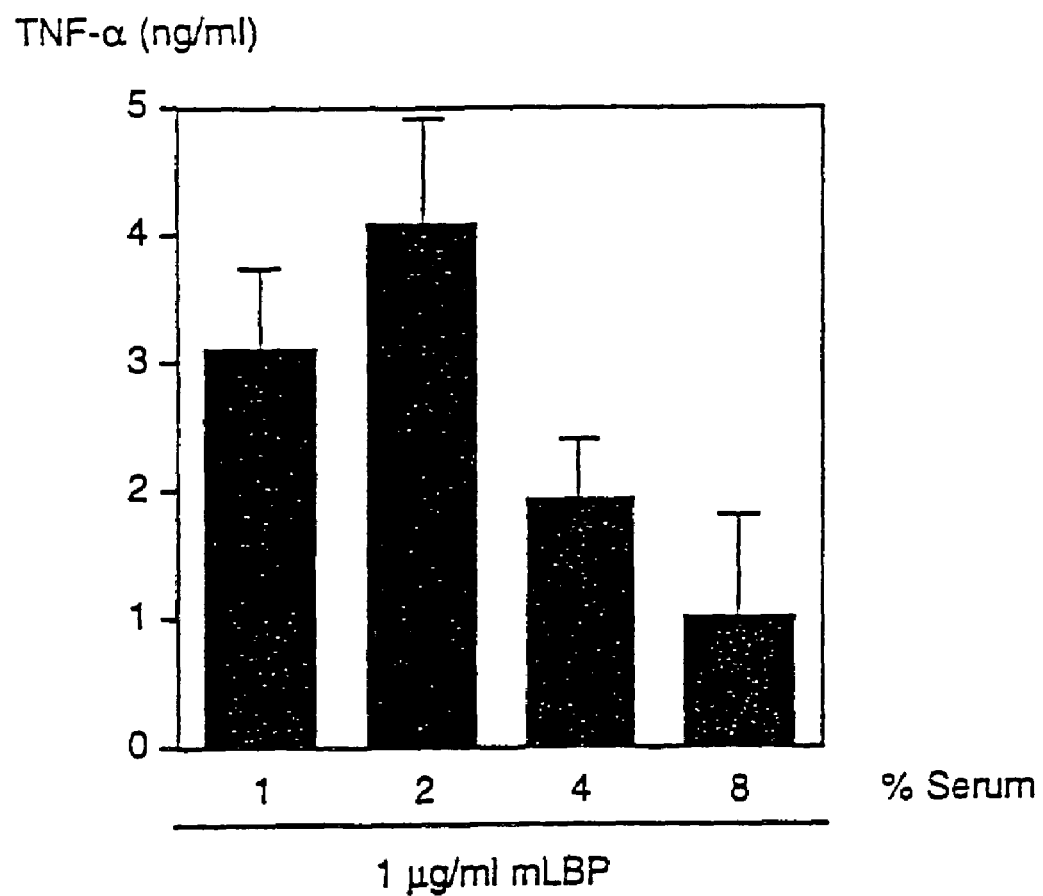
FIG. 3: If the concentration of serum is increased with LBP added remaining constant the synthesis of TNF is also suppressed.
Figure 4:
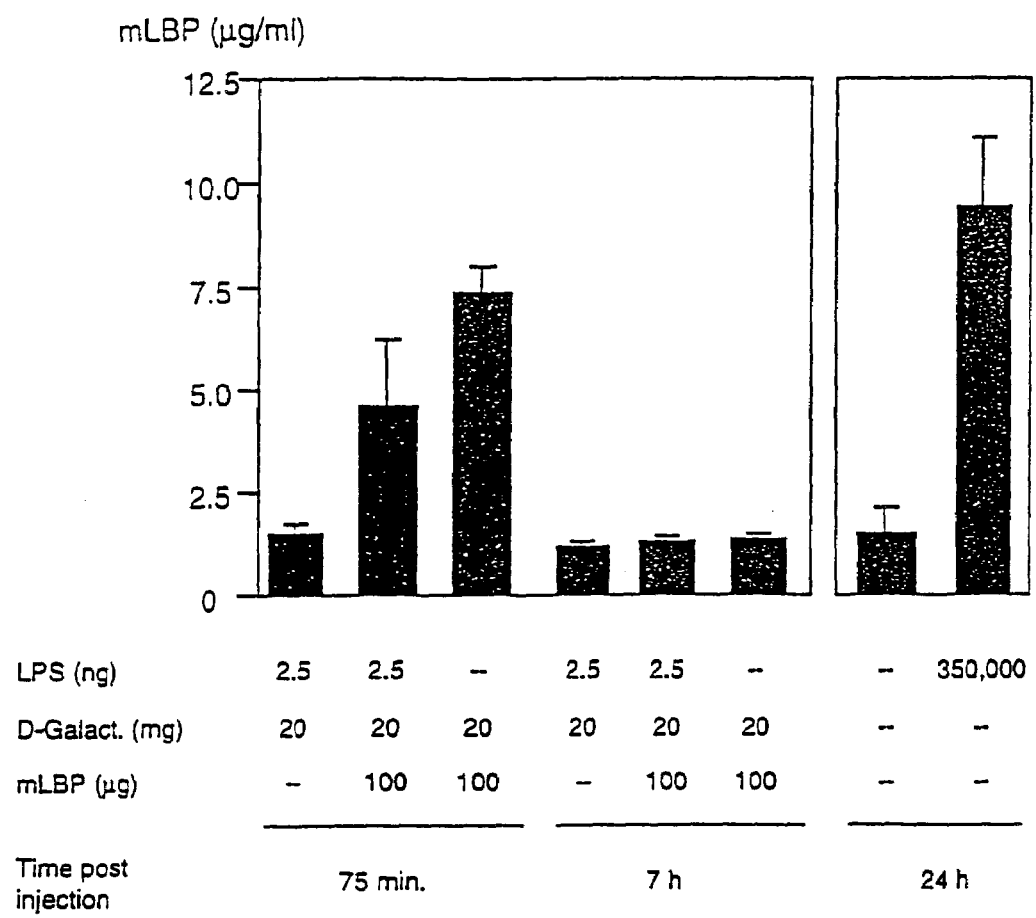
FIG. 4: Here it is shown that LBP levels of the mouse produced by an exogenous addition of LBP correspond to the acute phase levels produced by addition of LPS, thus being physiological.
Figure 5:
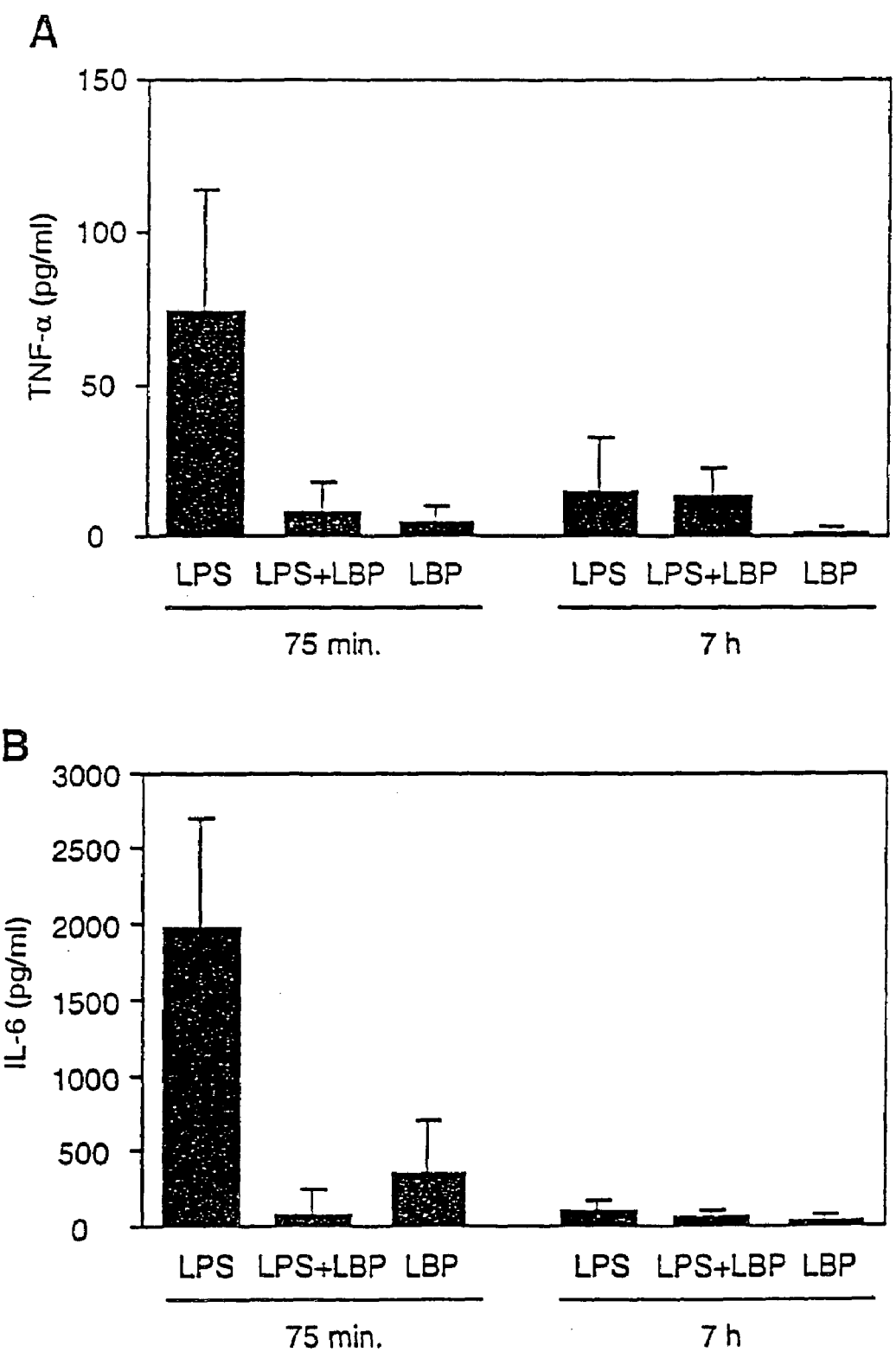
FIGS. 5A and 5B: Cytokine release induced by LPS may be suppressed in the mouse by simultaneously adding LBP. A: TNF, B: IL-6.
Figure 6:
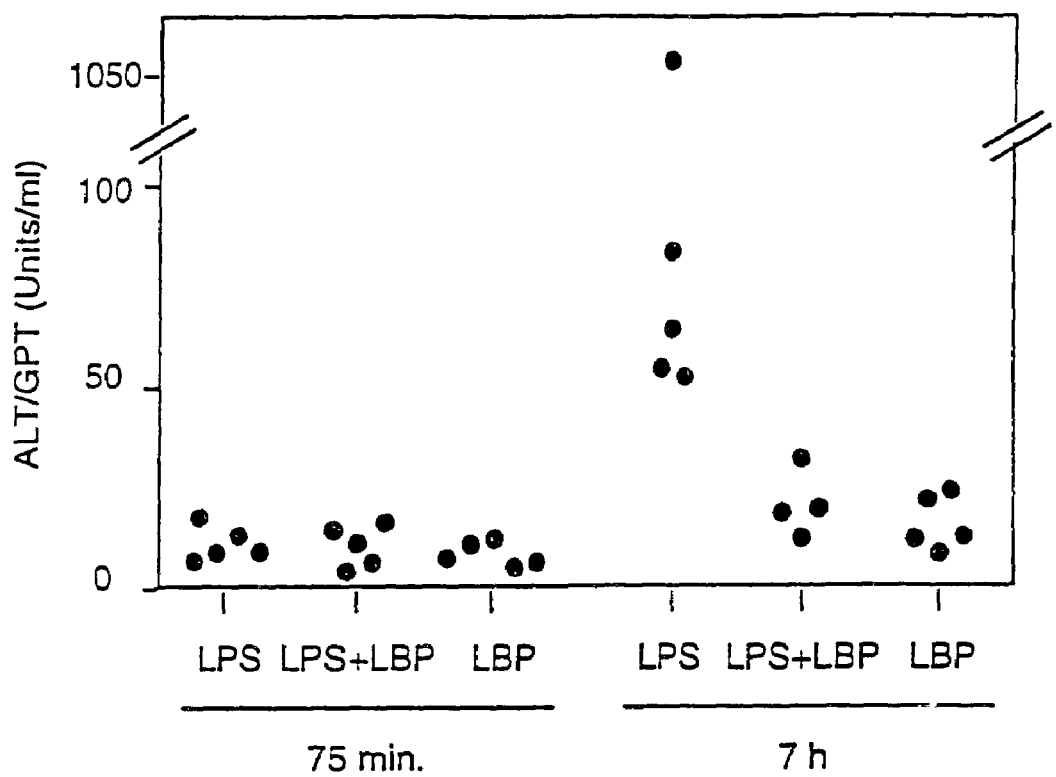
FIG. 6: In addition, the liver damage caused by LPS and detected by increasing ALT enzyme levels are suppressed by simultaneously adding LBP.
Figure 7:
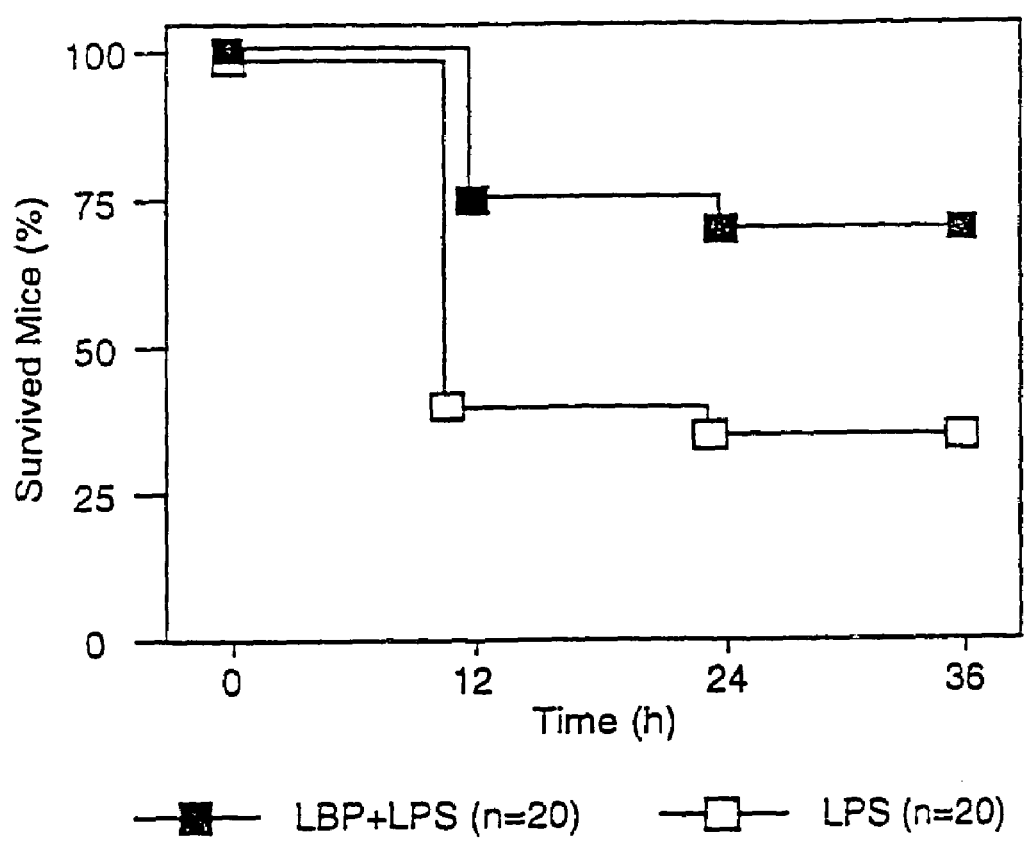
FIG. 7: The addition of LBP reduces significantly the lethality in a LPS septicemia model, carried out with 20 mice per group.

The structure of LBP is known. It was obtained by isolating a clone from an acute phase cDNA gene bank and subsequently sequencing and deriving the amino acid sequence. Recombinant LBP is prepared by cloning cDNA in an expression vector and co-infection of insect cells with the baculovirus.

The cloned protein (LBP) binds LPS with high affinity and is secreted into serum as acute phase protein during septicemia. As is shown in the examples LBP inhibits the LPS effects and may—if given to mice—suppress septicemia caused by LPS and reduce lethality highly significantly. This applies when using LBP simultaneously with the onset of septicemia and before. Thus LBP may seem to be suited for preventing septicemia in high-risk patients also. As LPS plays a central part also in septicemia caused by gram-positive bacteria and for the systemic inflammatory response syndrome, a clinical picture identical to septicemia caused by trauma, via translocation of gram-negative intestinal flora, the inhibition of LPS effects by LBP may also improve these dramatic clinical syndromes.

Apart from the highly active recombinant LBP optimized mutants the function of which was modified which are also used as therapeutic agents for the treatment of septicemia are equally suited for implementing the invention.

A further basic possibility for implementing the invention is to clone the LBP gene in an adenoviral vector with high activity in the liver behind the strong CMV promoter to achieve high levels of expression in addition to the intrinsic hepatic expression of LBP.

The invention is applicable in the case of
septicemia caused by gram-negative bacteria
septicemia caused by gram-positive bacteria
systemic inflammatory response syndrome (SIRS) caused by trauma and injury.

EXAMPLE

Hereinafter the invention shall be explained in greater detail by an example.

The complete LBP cDNA is cloned in the pACHLT-B vector (Pharmingen, San Diego, USA) behind the strong polyhedrin promoter and behind glutathione S-transferase (GST) cDNA. Thus a GST fusion protein is expressed. Then a 500 ml cell culture of Sf-9—insect cells is infected with this vector and the baculovirus DNA (Baculogold, Baculovirus DNA in a linearized form, also from Pharmingen, San Diego, USA). After 2 days the cells are subjected to lysis and the lysate is coupled to glutathione sepharose in the presence of triton X-100 in a "batch" process. Then LBP is split off by the participant in the fusion by digestion with thrombin followed by a treatment with calbiosorb to remove triton and a treatment with benzamidine sepharose to remove thrombine rests. The resulting concentrations of pure LBP totals 0.3–0.5 mg/ml.

Short Interpretation:

Highly dosed LBP in vitro suppresses the synthesis of an important septicemia mediator molecule caused by the bacterial toxin LPS, namely TNF. The production of this protein and other mediators is suppressed in the mouse by simultaneously adding LBP. In addition, the liver damage induced by the addition of LPS is prevented by LBP and the number of surviving mice goes up significantly. That means, the addition of LBP seams to protect against the effects of LPS during septicemia, representing thus a new therapeutic principle for treating septicemia.

What is claimed is:

1. A process for detoxifying bacterial lipopolysaccharide in a patient with septicemia caused by gram-negative bacteria or by gram-positive bacteria, which comprises administering to said patient an effective amount of lipopolysaccharide binding protein to elevate the serum concentration of lipopolysaccharide binding protein in said patient to a sufficiently high level to suppress lipopolysaccharide induced release of cytokine, thereby detoxifying the bacterial lipopolysaccharide.

2. The process of claim 1 wherein said lipopolysaccharide binding protein is a native or a recombinant lipopolysaccharide binding protein.

3. The process of claim 1, wherein said lipopolysaccharide binding protein is of human, rabbit, murine or rat lipopolysaccharide binding protein.

* * * * *